United States Patent
Crosato

(10) Patent No.: US 9,422,515 B2
(45) Date of Patent: Aug. 23, 2016

(54) FERMENTATION METHOD AND APPARATUS ADAPTED FOR THE METHOD

(75) Inventor: Remo Crosato, San Biagio di Callalta (IT)

(73) Assignee: L.A.S.I. S.R.L., Meolo (Venezia) (IT)

( * ) Notice: Subject to any disclaimer, the term of this patent is extended or adjusted under 35 U.S.C. 154(b) by 756 days.

(21) Appl. No.: 13/255,662

(22) PCT Filed: Mar. 18, 2009

(86) PCT No.: PCT/EP2009/053188
§ 371 (c)(1),
(2), (4) Date: Sep. 9, 2011

(87) PCT Pub. No.: WO2010/105675
PCT Pub. Date: Sep. 23, 2010

(65) Prior Publication Data
US 2011/0318451 A1    Dec. 29, 2011

(51) Int. Cl.
C12G 1/022 (2006.01)
C12G 1/02 (2006.01)
C12F 3/02 (2006.01)
C12M 1/107 (2006.01)
C12M 1/02 (2006.01)
C12M 1/00 (2006.01)

(52) U.S. Cl.
CPC ... C12G 1/02 (2013.01); C12F 3/02 (2013.01); C12M 23/36 (2013.01); C12M 27/00 (2013.01); C12M 29/24 (2013.01)

(58) Field of Classification Search
CPC ............ C12G 1/02; C12F 3/02; C12M 23/36; C12M 27/00; C12M 29/24
USPC ................................ 426/11, 15, 494; 99/276
See application file for complete search history.

(56) References Cited

U.S. PATENT DOCUMENTS 4,908,219 A    3/1990    Modot et al.

FOREIGN PATENT DOCUMENTS

| AT | 005 698 U1 | 10/2002 |
| EP | 0 300 900 A1 | 1/1989 |
| EP | 0 737 740 A1 | 10/1996 |
| EP | 1 314 778 A1 | 5/2003 |
| EP | 1 964 914 A1 | 9/2008 |
| EP | 2 058 384 A1 | 5/2009 |
| EP | 2 060 623 A1 | 5/2009 |
| WO | WO 98/45403 A1 | 10/1998 |
| WO | WO 2004/091764 | 10/2004 |
| WO | WO 2005/023977 A1 | 3/2005 |
| WO | WO 2006/087601 A1 | 8/2006 |

*Primary Examiner* — Vera Stulii
(74) *Attorney, Agent, or Firm* — Birch, Stewart, Kolasch & Birch, LLP

(57) ABSTRACT

A method for treating a vegetable product in the form of crushed material includes the steps of (i) storing the crushed material in a first vat to let it ferment and form a cap of solid parts floating on a liquid mass therein; (ii) connecting a second vat to the first one to gather in it the gaseous products generated due to fermentation; (iii) isolating the two vats; (iv) reducing the gaseous pressure in the first vat; (v) connecting the second vat to the first at a point beneath the cap so that, due to the differential pressure between the two vats, spontaneous racking of gaseous products in the liquid mass occurs, in such a manner that rising they get into contact with the cap.

11 Claims, 2 Drawing Sheets

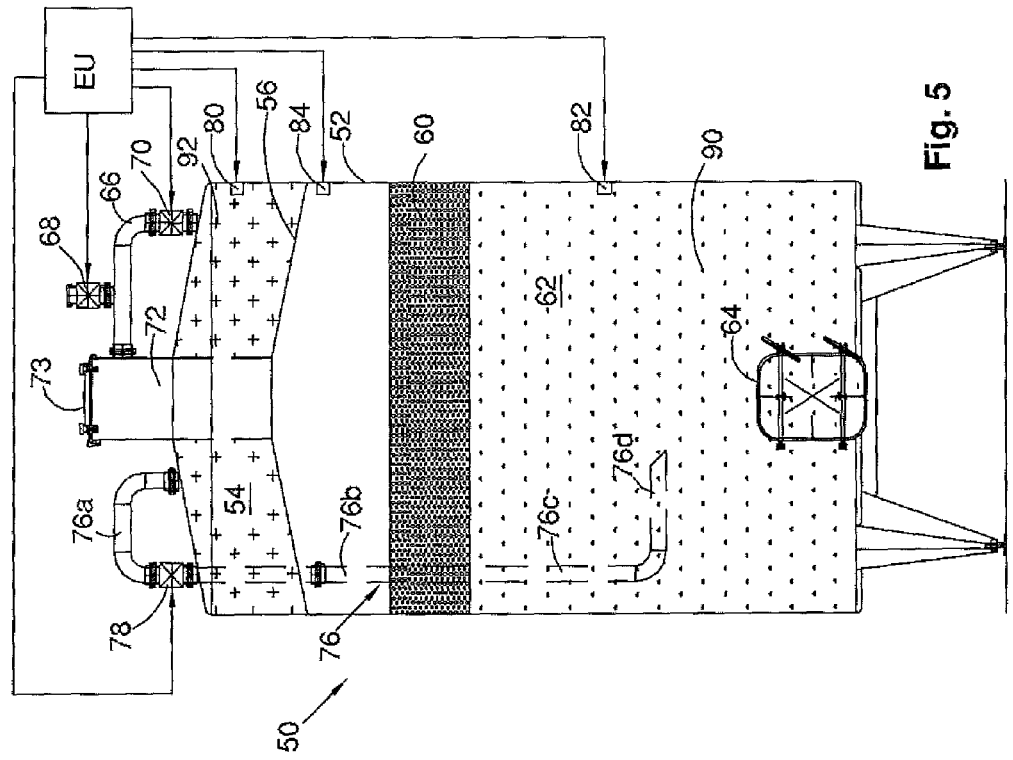
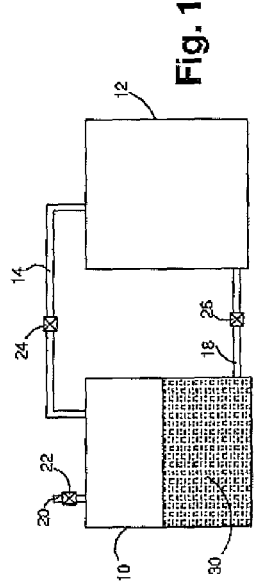
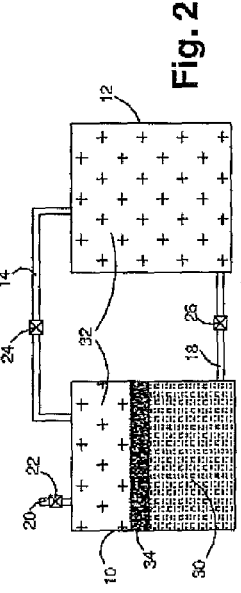
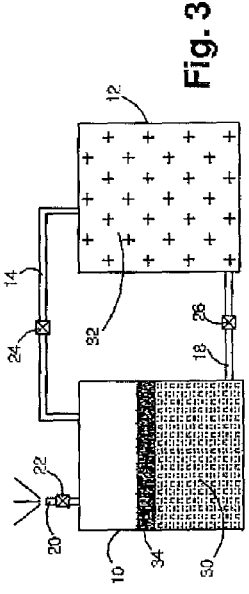
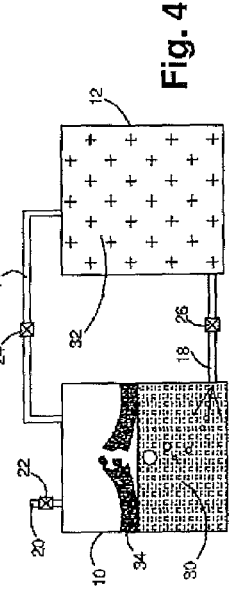

FERMENTATION METHOD AND APPARATUS ADAPTED FOR THE METHOD

The invention regards a fermentation method and an apparatus adapted to implement the method. Though the invention is useful for the treatment of any vegetable product in the form of crushed material, the subsequent description shall refer in an exemplifying manner to winemaking, field in which the invention proved particularly efficient.

Winemaking occurs with the aid of special vats where the must is introduced for fermentation. The fermentation process generates a large amount of gaseous products, especially $CO_2$, which participate actively in the production of good quality wine. The gases are released by the must and they push the mare and any other solid particles towards the top where they compact and form a solid layer, known as "cap".

Winemaking methods suitably exploit the fermentation gases. WO 2006/087601 describes a winemaking vat which controls the pressure of the gases within it, regulating it to an almost constant value.

In WO 98/45403 the gases exploited to remix the cap and prevent it from solidifying. A fermenter vat is described, provided within it with an inclined diaphragm under which the gas accumulates and then constantly flows, in the form of bubbles, towards the floor of the cap. The bubbles agitate and keep it mixed. A valve and an external pipe allow quick evacuation of the gas accumulated under the diaphragm to discharge it under the cap.

This invention has various disadvantages including the fact that:
- the gas volume accumulated depends on the size of the diaphragm, and it depends on the overall volume of the fermenter;
- as the gas accumulates, the cap raises upwards, and it requires supervision to avoid overflowing;
- even the mare finds its way under the diaphragm, thus there it can encrust creating serious cleaning problems, it can clog the pipe and the external valve; and definitely limits the amount of gas which can be accumulated.

The object of the present invention is to provide a method and an apparatus for the treatment of a vegetable product in the form of crushed material, preferably must, capable of exploiting gases produced during fermentation without the above-mentioned drawbacks.

Such object is obtained by means of a method for the treatment of a vegetable product in the form of crushed material comprising the steps of
(i) Storing the crushed material in a first vat to let it ferment therein and to form a cap of solid particles floating on a liquid mass;
(ii) Connecting a second vat to the first for gathering the fermentation gas products in it;
(iii) Isolating the two vats;
(iv) Reducing the gaseous pressure in the first vat;
(v) Connecting the second vat to the first at a point beneath the cap so that, thanks to the differential pressure between the two vats, spontaneous pouring off (also definable as discharge or release) of the gaseous products in the liquid mass occurs, in such a manner that while rising they get into contact with the cap.

Thus, exploiting the natural gas generated by the fermentation, the cap can be broken.

The preferred variants, separate or combined, of the method are:
- the second vat is connected to the first one in such a manner that gathering of the gaseous products occurs by means of spontaneous migration of the gases (advantageous absence of actuators or pumps);
- steps (ii) to (v) are performed in a cyclic manner according to a preset program (automation of the system);
- in step (iv) the gaseous pressure in the first vat is reduced up to room pressure (simple venting);
- in step (iv) the gaseous pressure in the first vat is reduced to an intermediate pressure value between the one of the second vat and the room pressure one (a more sophisticated pressure control operation);
- in step (v) pouring off is performed in only one time, substantially involving the entire content of the second vat (for maximum effect on the cap);
- in step (v) pouring off is performed by means of repeated preset-flow impulses, involving each time fractions of the content of the second vat (for a more delicate and/or prolonged breakage of the cap);
- the gaseous pressure is controlled in the second vat and step (v) is performed when such pressure exceeds the preset threshold (thus leading to a controlled and safe process);
- the level of the of the crushed material in the first vat is controlled and in case the point beneath the cap at which the gaseous products are released into step (v) is varied to ensure that said gaseous products run into the cap from beneath (thus leading to a controlled and safe process);

The method of the invention can be implemented by an apparatus for the treatment of a vegetable product in the form of crushed material useful for implementing the method of the preceding claims, comprising
- a first vat for containing the crushed material and a second collection vat for gathering gaseous products generated from the crushed material's fermentation;
- a first piping system adapted to let communicate a part of the first vat, where the gaseous products accumulate, with the second vat;
- a second piping system adapted to let communicate the second and the first vat, the system being provided with an outlet inside the first vat where, in use, the liquid mass of the crushed material is present;
- first and second valve means respectively associated to the first and second piping system to make the two vats selectively communicating depending on the open/closed status of said means.

Preferred variants, separate or combined, of the apparatus are that:
- it comprises third valve means for degassing the first vat towards the outside;
- it comprises an external shell partitioned internally by at least one separation wall into two sub-volumes which constitute said first and second vat;
- said first and second vat are arranged vertically one over the other inside the shell;
- it comprises two independent separation walls for delimiting said two sub-volumes, the two walls being concave and arranged with the concavities facing opposite directions;
- the first piping system comprises an external pipe with respect to the shell in series of which an adjustable valve is mounted;
- it comprises a programmable processing device programmed for controlling the valve means in such a manner to perform, after loading a vegetable product in the form of crushed material into the first vat, the steps of
(i) connecting the second vat to the first one to gather in it the gaseous products, generated by fermentation, by opening the first valve means;

(ii) closing the first and second valve means so as to isolate the two vats;

(iii) open the second valve means to connect the second vat to the first one in such a manner that spontaneous pouring off of the gaseous products in the liquid mass of the crushed material occurs;

the processing device is programmed to reduce the gaseous pressure in the first vat by operating the third valve means;

the processing device is programmed to open the second valve means only one time, in such a manner to let the gases move from one vat to the other substantially involving the entire content of the second vat;

the device is programmed to open the second valve means with repeated impulses in such a manner that the gases move from one vat to another through preset flow-rate packets.

The invention also regards a program for the said programmable device such that, when loaded into and run by the programmable device, the program manages the control of said valve means and/or reading of the said sensors.

BRIEF DESCRIPTION OF DRAWINGS

FIGS. 1-4 show the principle of the invention by means of a diagram.

FIG. 5 shows a preferred embodiment of a winemaking apparatus.

Figure 6:
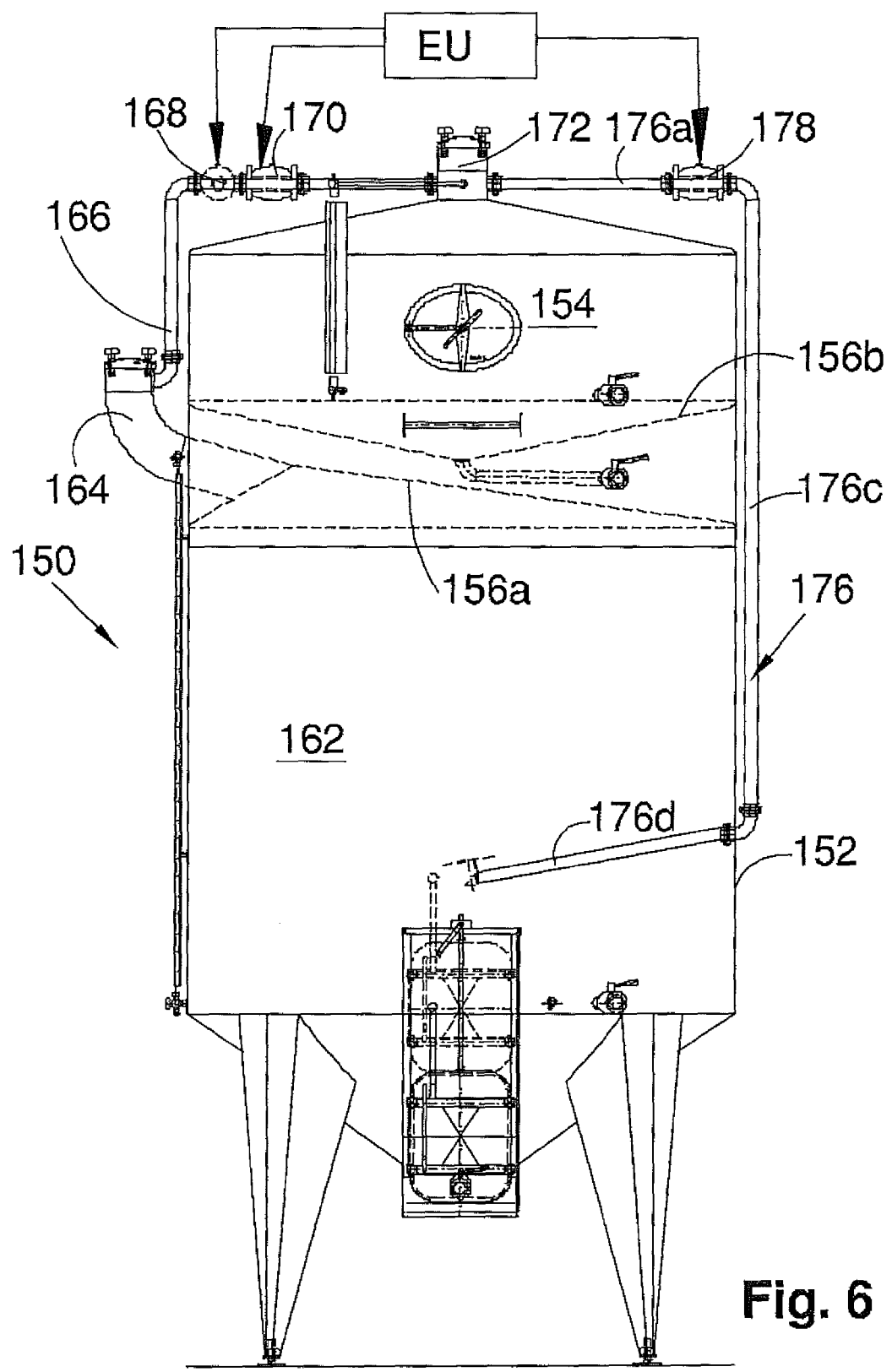
FIG. 6 shows another preferred embodiment of a winemaking apparatus.

Now, reference shall be made to FIGS. 1-4, which show the principle of the invention by means of a diagram.

A vat or winemaking apparatus 10 (FIG. 1) is filled with must 30 through known means and methods. A pipe 14 puts into communication in a controllable manner, by means of a valve 24, the upper part of the vat 10 to the upper part of a second vat 12. A second pipe 18 puts into communication in a controllable manner, by means of a valve 26, the lower part of the vat 10 to the upper part of the vat 12. The vat 10 has an upper vent 20 controllable by means of a valve 22. The valve 26 is initially closed in such a manner to prevent backflow of the must 30.

After a given period of time (FIG. 2) the must 30 under fermentation generates gaseous products or gas 32 (especially $CO_2$) and leads to the formation of a solid cap 34. It should be observed that the pipe 18 ends up into the vat 10 at a point occupied by the must 30, at a level below the bottom of the cap 34. The valve 24 is opened and the gas 32 spontaneously flows into the vat 12. The valve 22 is closed to prevent gas 32 from leaking from the vat 10.

After a preset period of time, the vats 10, 12 are isolated by closing the valve 24. The gas 32 remains trapped under pressure in the vat 12, while the other is depressurised (or degassed) through the pipe 20 by opening the valve 22 (FIG. 3).

The pressure of the gas 32 in the isolated vat 32 can be controlled in the preceding step by means of the valve 22, for example using one having an opening calibrated threshold. A value proved experimentally advantageous ranges between 0.3 and 2 bars (such value shall be established from time to time by the user and depending on the type of grapes/must alongside the final product the winemaker strives to obtain: therefore, should the products treated according to this invention require it, higher or lower pressures with respect to the ones indicated and usually used could be applied). The valve 22 also allows the adjustment of the residue pressure in the vat 10 after degassing; re-establishing the atmospheric pressure was proved experimentally advantageous and simple.

Lastly, (FIG. 4), the valve 26 is opened and the gas 32 spontaneously flows into the must 30. Rising, the gas 32 shall determine delicate breakage of the cap 34 and its leaching extracting its aromas and natural pigments.

As mentioned, among the variants of the method, the main ones are that:

the steps described above can occur cyclically at fixed or variable intervals;

degassing of vat 10 occurs by restoring its interior to atmospheric pressure or leaving it at an intermediate pressure between the latter and the one in the vat 12;

the gas 32 can be released into the vat 10 all in one time or at more or less prolonged impulses, controlling their flow rate every time.

Advantageously the components of FIGS. 1-4 are integrated in a single winemaking apparatus, described below with reference to the drawings attached, wherein FIGS. 1-4 show the steps of the method according to the invention;

FIG. 5 shows a preferred embodiment of the winemaking apparatus, indicated with 50;

FIG. 6 shows a second preferred embodiment of the winemaking apparatus, indicated with 150.

The winemaking apparatus 50 for holding must 90 is made up of a cylindrical shell 52 partitioned internally by a separation wall 56 shaped as a horizontal dome, into two sub-vats or superimposed volumes 54, 62, respectively upper and lower.

The lower volume 62 communicates to the outside by means of a base hatch 64 and a vertical hatchway 72, around which the vat 54 develops.

The upper vat 54 can be connected selectively to the hatchway 72 by means of a pipe 66 and a valve 70. The same pipe 66 is provided with a second valve 68 with the function of putting into communication the hatchway 72 to the outside (when its closing door 73 is closed).

The upper vat 54 can also be connected selectively to the lower vat 62 through a pipe 76 and a valve 78. The pipe 76 has an elbow section 76a which runs external to the shell 52, a vertical section 76b which runs through the upper vat 54, a vertical section 76c which passes through part of the lower vat 62 and a horizontal outlet section 76d.

The length of section 76c is such that, during the steps of the method, section 76d is always, also taking into account the expected level of the must 90, under the cap generated by the fermentation, indicated with 60. However, an adapting adjustment system, for example a telescopic pipe 76d which can be controlled from outside to adjust the height or level of section 76d, can be installed.

Control of the telescopic pipe or equivalent means for conveying the gas provided with a gas outlet with adjustable position in the in vat 62 can occur by means of a programmable processing device EU, for example a PC or PLC. This device can be provided with timers, programming user interfaces and driving stages for the valves 68, 70, 78 (see arrows in FIG. 5).

The device EU can be interfaced with a pressure sensor 80, which measures the pressure of the gas 92 in vat 54, and/or a pressure sensor 84, which measures the pressure of the gas present in vat 62, and/or a level sensor 82, which measures the level of the liquid in the vat 62.

The winemaking apparatus 50 operates as follows. Reference shall also be made to FIGS. 1-4 for correspondence with the details provided beforehand. In particular observe the correspondence between:

Vat 10←→Vat 62
Vat 12←→Vat 54
Valve 22←→Valve 68
Valve 24←→Valve 70
Valve 26←→Valve 78.

(i) Vat 62 is filled with must 90.

(ii) After a given period of time the must 90 under fermentation generates gas and a solid cap 60. Valve 70 is opened, valve 68 shall be regulated in such a manner to bring the two vats to a preset pressure and maintain it constant over a given period of time, valve 78 is closed. Thus, spontaneously, the gas flows into the vat 54 (see reference 92 in FIG. 5).

(iii) After a set period of time, valve 70 is closed. The gas 92 remains trapped under pressure in the vat 54, while the other vat 62 is depressurised (or degassed) by opening the valve 68.

(iv) The valve 78 opens and the gas 92 spontaneously flows into the must 30 and while rising it interacts with the cap 60, breaking it.

The steps of the process described above are preferably controlled by the device EU.

By reading and processing the data delivered by the sensor 80, the device EU can control the valves 68, 70, 78 to perform the steps of the method when for example a maximum threshold pressure is reached in the vat 54.

By reading and processing the data delivered by the sensor 82, the device EU can control the said telescopic pipe or equivalent means to convey in such a manner that in step (iv) it is always ensured that the gas 92 runs into the cap 60 from beneath. However, it can be attained that the cap 60 is hit by the gas 92 even for example at a point within its thickness.

It is clear that each step of the winemaking process of the invention can be advantageously automated and/or programmed. This allows, for example, to set periodic cycles of breakage of the cap 60, to experiment various methods of degassing the vat 10 (finding the best intermediate pressure value between the one in the vat 54 and the room pressure: the required value is obtained by controlling the data of the sensor 84 through the device EU), to program the parameters for releasing the gas 92 into the vat 10 (such as the duration of the single-discharge release or the duration of various consecutive impulses, the gas flow-rate per each impulse, etc.).

A second winemaking apparatus 150 is shown in FIG. 6. Its operation is identical to the previous one, thus only components substantially deferring from it in terms of construction (for example must and cap are not shown) will be indicated. Elements operatively analogous to the previous ones are indicated by the suffix "1". In practice, the piping systems conveying gas into and out of the gas gathering vat and the internal repartition of the external shell are made in a different manner.

The winemaking apparatus 150 is made up of a cylindrical shell 152 repartitioned internally by two separation walls having a horizontal dome 156a, b into two sub-vats or superimposed volumes 154, 162, respectively upper and lower. The lower volume 162 communicates with the outside through a vent 164.

The upper vat 154 is selectively connectable to the vent 164 through a pipe 166 and a valve 170.

A valve 168 on the pipe 166 has the function of making communicating the vent 164, and thus the vat 162, to the outside and of regulating the pressures inside the vats.

The upper vat 154 is also selectively connectable to the lower vat 162 through a pipe 176 and a valve 178. The pipe 176 has an elbow section 176a which runs above and external to vat 154, a vertical section 176b which runs external to vats 154, 162, and an almost horizontal outlet section 176d which extends inside vat 162, with the outlet approximately at the centre of the vat itself and at a point, with the must present, beneath the cap.

As described previously, a programmable device EU manages the automatic driving of the valves 168, 170, 178.

For simplicity purposes, the pressure and/or level sensors described above, which perform the same functions as already mentioned beforehand, are not shown.

The operation of the winemaking apparatus 150 is conceptually analogous to the previous one and it is not repeated. Obviously, all the observations expressed regarding the winemaking apparatus 50 remain valid. In particular, the functional correspondence between the components of the winemaking apparatus 50, 150 should be observed:

Vat 62←→Vat 162 (must containment)
Vat 54←→Vat 154 (gas containment)
Valve 68←→Valve 168 (for degassing the must containing vat)
Valve 70←→Valve 170 (for gathering gas between the two vats)
Valve 78←→Valve 178 (for discharging gas form one vat to the other).

It goes without saying that some construction details, as described beforehand, of the winemaking apparatuses 50, 150 can also be omitted, or arranged combined with each other in other different embodiments.

The invention claimed is:

1. A method for the treatment of a vegetable product in the form of crushed material comprising the steps of:
   (i) storing the crushed material in a first vat to let it ferment and form a cap of solid particles floating on a liquid mass therein;
   (ii) connecting a second vat to the first vat and transferring the gaseous products of fermentation, accumulated in the first vat and generated by fermentation, to the second vat;
   (iii) isolating the first and second vats;
   (iv) reducing the gaseous pressure in the first vat; and
   (v) connecting the second vat to the first vat at a point beneath the cap so that, due to the differential pressure between the first and second vats, spontaneous pouring off of the gaseous products in the liquid mass occurs, in such a manner that while rising the gaseous products come into contact with the cap.

2. The method according to claim 1, wherein the second vat is connected to the first vat in such a manner that gathering of the gaseous products occurs due to spontaneous migration of the gases.

3. The method according to claim 1, wherein steps (ii) to (v) are performed cyclically according to a preset program.

4. The method according to claim 1, wherein in step (iv) the gaseous pressure in the first vat is reduced until the pressure reaches room pressure.

5. The method according to claim 1, wherein in step (iv) the gaseous pressure in the first vat is reduced until the pressure reaches an intermediate pressure value between the pressure of the second vat and the room pressure.

6. The method according to claim 1, wherein in step (v) pouring off is performed in only one time, substantially involving all the content of the second vat.

7. The method according to claim 1, wherein in step (v) pouring off is performed through repeated preset-flow impulses, involving from time to time fractions of the content of the second vat.

8. The method according to claim 1, wherein the gaseous pressure in the second vat is controlled and step (v) is performed when such pressure exceeds a preset threshold.

9. The method according to claim 1, wherein the level of the crushed material in the first vat is controlled and in case the point beneath the cap at which the gaseous products are released in step (v) is varied to ensure that said gaseous products run into the cap from beneath.

10. The method according to claim 1, wherein must is used as the crushed product.

11. A method for the treatment of a vegetable product in the form of crushed material comprising the steps of:
   (i) storing the crushed material in a first vat to let it ferment and form a cap of solid particles floating on a liquid mass therein;
   (ii) transferring fermentation gases from the first vat to the second vat by a first pipe, the first pipe extending between an upper portion of the first vat with an upper portion of the second vat;
   (iii) isolating the first and second vats;
   (iv) reducing gaseous pressure in the first vat; and
   (v) connecting the second vat to the first vat at a point beneath the cap with a second pipe, the second pipe extending between a lower portion of the first vat with a lower portion of the second vat so that, due to the differential pressure between the first and second vats, the fermentation gases from the second vat rise through the first vat to come into contact with the cap.

* * * * *